United States Patent [19]

Avnir et al.

[11] Patent Number: 6,159,453
[45] Date of Patent: Dec. 12, 2000

[54] SUNSCREENS FOR PROTECTION FROM SUN RADIATION

[75] Inventors: David Avnir, Jerusalem, Israel; Levy David Cohen, Madrid, Spain

[73] Assignee: Yissum Research Development Company of the Hebrew University of Jerusalem, Jerusalem, Israel

[21] Appl. No.: 09/341,647

[22] PCT Filed: Jan. 15, 1998

[86] PCT No.: PCT/IL98/00021

§ 371 Date: Jul. 15, 1999

§ 102(e) Date: Jul. 15, 1999

[87] PCT Pub. No.: WO98/31333

PCT Pub. Date: Jul. 23, 1998

[30] Foreign Application Priority Data

Jan. 16, 1997 [IL] Israel ......................................... 120022

[51] Int. Cl.⁷ ............................... A61K 7/42; A61K 7/44; A61K 7/00; A61K 9/48; A61K 9/66
[52] U.S. Cl. ............................ 424/59; 424/60; 424/401; 424/451; 424/455; 424/489; 424/490; 501/12; 501/32; 501/53
[58] Field of Search ............................... 424/401, 59, 60, 424/457, 455, 489, 490; 501/12, 53, 32

[56] References Cited

U.S. PATENT DOCUMENTS

| | | | |
|---|---|---|---|
| 5,223,250 | 6/1993 | Mitchell et al. | 424/59 |
| 5,300,564 | 4/1994 | Avnir et al. | 525/54.1 |
| 5,316,854 | 5/1994 | Lin et al. | 428/426 |
| 5,587,170 | 12/1996 | Caisey et al. | 424/401 |
| 5,601,807 | 2/1997 | Asaoka | 424/59 |
| 5,817,160 | 10/1998 | Nagpal et al. | 65/17.3 |

FOREIGN PATENT DOCUMENTS 0 281 034  9/1988  European Pat. Off. .

OTHER PUBLICATIONS (1) Patent Abstract of JP 08 099838, Aug. 30, 1996.
(2) Chemical Abstract of JP 07 315 859, May 12, 1995.
(3) Chemical Abstract of JP 05 178 995, Jul. 20, 1993.

*Primary Examiner*—Shelley A. Dodson
*Assistant Examiner*—Marina Lamm
*Attorney, Agent, or Firm*—Lowe Hauptman Gopstein Gilman & Berner, LLP

[57] ABSTRACT

The present invention relates to sunscreen-doped sol-gel materials useful for protecting body tissues, such as skin, nails and hair and other surfaces from sunlight radiation. The sol-gel matrices are transparent to the UV radiation in the range above 250 nm and the doped sunscreen agents are either chemical or physical sunscreens capable of absorbing the UV radiation in the range above 250 nm. Any sunscreen molecule, moiety or particle may be used in the present invention. The sol-gel matrices may be particles in any shape, 0.01–100 microns in diameter, or they may be thin films, thin coatings or in the form of a monolith. The present invention also relates to a method for the preparation of sunscreen-doped sol-gel materials comprising condensation-polymerizing of at least one monomer selected from metal alkoxides, semi metal alkoxides, metal esters, semi metal esters and from monomers of the formula $M(R)n(P)m$, wherein M is a metallic or semi metallic element, R is a hydrolyzable substituent, n is an integer from 2 to 6, P is a non polymerizable substituent or a sunscreening moiety or derivative and m is an integer from 0 to 6, in the presence of at least one sunscreen ingredient, resulting in the entrapment of the sunscreen ingredients within the formed sol-gel matrix.

20 Claims, No Drawings

SUNSCREENS FOR PROTECTION FROM SUN RADIATION

This application is a 371 of PCT/IL98/00021 filed Jan. 15, 1998.

FIELD OF THE INVENTION

The present invention generally relates to sunscreen-doped sol-gel materials useful for protecting body tissues and other surfaces from ultra violet radiation (the term "ultra violet radiation" in the present invention, unless otherwise specified, includes radiation in the range of 320–400 nm, called UVA, and radiation in the range of 280–320 nm, called UVB. Ultra violet radiation is hereinafter called UV radiation), to a method for preparing said sunscreen-doped sol-gel materials and to a method for protecting body tissues and other surfaces from UV radiation, using the said sunscreens. More specifically, the present invention relates to sol-gel matrices produced by hydrolysis and condensation-polymerization of metal and semi-metal alkoxide monomers to which sunscreen molecules are added either prior to or after hydrolysis of the monomer, followed, if needed, by a pH change and by gelation. The resulting sunscreen-doped sol-gel materials can be obtained in almost any shape and may be applied, as dispersions or powders, to body tissues and other surfaces, thereby achieving protection of the body tissues and surfaces against damaging effects of the sun radiation, without having undesirable direct contact between the sunscreening chemical ingredients and the body tissues.

BACKGROUND OF THE INVENTION

Sunscreens are chemical ingredients which are usually applied topically to the skin and hair in order to protect them from the damaging effects of the sun's radiation, especially against (UV) ultraviolet radiation.

There is evidence that prolonged sunlight exposure results in increasing incidence of skin carcinogenesis, pigmentation, anomalies and precancerous lesions such as actinic keratosis, melanoma and nonmelanoma skin cancers, as well as accelerated skin aging and undesirable changes in hair quality.

Sunscreens are usually classified in two major categories. The first includes chemical sunscreens which absorb sun radiation and therefore reduce the amount of UV radiation reaching the skin. Chemical sunscreens can be subdivided into eight derivative families: para amino benzoates, salicylates, cinnamates, benzophenones, anthranilates, dibenzoylmethanes, camphores and miscellaneous chemicals. The second category includes physical sunscreens which reflect, scatter or physically block the UV light reaching the skin surface. Physical sunscreens are mainly metal oxides such as titanium dioxide, zinc oxide and also red petrolatum.

Ultimate sunscreens should be chemically inert, highly photostable and neither sensitizing nor photosensitizing. Yet, according to more than 200 published reports relating to all major chemical sunscreen families, sunscreen agents induce both contact and photocontact dermatitis (Dromgoole and Maibach, In Sunscreens, eds. N. J. Lowe, N. A. Saath; Marcel Dekker: N.Y., 1990, Chapter 20). In other publications it was reported that commonly used sunscreen compounds undergo photodecomposition reactions (Roscher et al. J. Photochem. Photobiol. A: Chem, 80: 417–421, 1994). Moreover, although more people are using sunscreens, the rate of skin cancer around the world is rising. A possible explanation is that sunscreens might encourage, rather than prevent, sun related cancers. Indeed, it was found (Knowland et al. FEBS Letters, 324: 309–313, 1993) that the commercial sunscreen ingredient Padimate-O is mutagenic in sunlight. The sunlight-excited Padimate-O is thought to produce free radicals which directly attack the DNA.

Physical sunscreens, especially titania, such as disclosed in Chemical Abstracts 124:153660 although considered to be "relatively safe", are known to be photosensitizers capable of rupturing covalent bonds (U. Stafford, K. A. Gray and P. V. Kamat, Heterogeneous Chem Rev, 3, 77–104, 1996).

There is, therefore, a great need for isolating chemical and physical sunscreen agents from the body while retaining both the sunscreen activity and the compatibility with cosmetic preparations.

U.S. Pat. No. 5,223,250 and WO Patent 95/28912 describe the entrapments of sunscreen ingredients in organic polymers. However, organic polymers suffer a major drawback in that they do not provide photostability, a most important requirement of a sunscreen matrix. The photodegradation, photooxidation and photoreactivity of organic polymers are well documented (summarized in J. F. Rabeck, Photodegradation of polymers; Springer: Berlin, 1996). Also, plastic carriers, as in the above mentioned patents, are unable to tightly entrap dopants. Small molecules are known to diffuse in and out of these polymers, making the isolation from body tissues incomplete.

The present invention relates to sunscreen-doped sol-gel materials, such as chemical and physical sunscreens that are doped in a transparent sol-gel matrix, for the purpose of protecting body tissues (the term "body tissues" in the present invention refers to body tissues that are exposed to sun light such as hair, skin and nails) and other surfaces (the term "surfaces" in the present invention refers to surfaces that are exposed to sun light and may be damaged from the exposure to UV radiation) from ultra violet (UV) radiation, to a method for the preparation of these sunscreen-doped sol-gel materials and to a method for the protection of body tissues and other surfaces exposed to sunlight, from UV radiation, using the said sunscreens.

In the present invention the term "sunscreen-doped sol-gel" refers to sunscreen molecules or polymers (capable of absorbing or deflecting UV radiation) when they are doped in sol-gel matrix.

The term "chemical sunscreen" in the present invention refers to chemical ingredients which absorb sun radiation and therefore reduce the amount of UV radiation reaching the skin or other surfaces. The term "physical sunscreens" in the present invention refers to chemical ingredients which reflect, scatter or physically block the UV light reaching the skin or other surfaces.

U.S. Pat. Nos. 5,292,801 and 5,300,564 (inventors: Avnir et al) describe the preparation of the inorganic porous ceramic glass-like sol-gel matrix obtained by hydrolysis and condensation-polymerization of metal and semi metal alkoxides resulting in oxide-type materials such as $SiO_2$, $TiO_2$, $Al_2O_3$, ZnO and similar materials, as well as in their mixtures and their covalent bound organic derivatives. Due to the relatively low temperature needed for the preparation of sol-gel matrices, organic molecules can be doped into the matrix.

Sol-gel matrices doped with organic molecules are disclosed for example in EP 0281034 in which the organic molecules are perfume molecules and in Patent Abstracts of Japan Publication No. 08099838 in which the organic molecules are color molecules.

The sol-gel matrix of the present invention is thermally and photochemically stable, as opposed to the above mentioned (U.S. Pat. No. 5,223,250 and WO 95/28912) plastic carriers, and can easily withstand normal duration of exposure to sunlight. Also, as opposed to the plastic carriers of the above patents, no leaching of the trapped sunscreen agents occurs from the sol-gel matrix, so that there is no direct contact of the sunscreen molecules with the body tissues.

The present invention relates to a simple method for preparing a matrix entrapping any sunscreen molecule or particle, providing, for the first time, a stable, safe and environment friendly sunscreen.

SUMMARY OF THE INVENTION

The present invention relates to sunscreen-doped sol-gel materials useful for protecting body tissues, such as skin, nails and hair and other surfaces from sunlight radiation.

The sol-gel matrices are transparent to the UV radiation in the range above 250 nm and the doped sunscreen agents are either chemical or physical sunscreens capable of absorbing the UV radiation in the range above 250 nm. Chemical sunscreens may be para amino benzoates, salicylates, cinnamates, benzophenones, anthranilates, dibenzoylmethanes, camphores and physical sunscreens may be titanium dioxide, zinc oxide and red petrolatum. This invention is not limited in any way to the given examples of sunscreening agents. Any sunscreen molecule, moiety or particle may be used in the present invention. The sol-gel matrices may be particles in any shape, 0.01–100 microns in diameter, or they may be thin films, thin coatings or in the form of a monolith.

The present invention also relates to a method for the preparation of sunscreen-doped sol-gel materials comprising condensation-polymerizing of at least one monomer selected from metal alkoxides, semi metal alkoxides, metal esters, semi metal esters and from monomers of the formula M(R)n(P)m, wherein M is a metallic or semi metallic element (such as silicon, titanium, zinc, aluminum, zirconium) R is a hydrolyzable substituent (such as alkoxides, aryloxides, carboxylic esters, acyloxy groups, diketonato groups, hydrolizable aza groups and chlorine), n is an integer from 2 to 6, P is a non polymerizable substituent or a sunscreening moiety or derivative and m is an integer from 0 to 6, in the presence of at least one sunscreen ingredient, resulting in the entrapment of the sunscreen ingredients within the formed sol-gel matrix.

Preferably, the sunscreen ingredients are added to the polymerizing mixture, either prior to or after hydrolysis of the monomer, followed, if needed, by a pH change and by gelation. The polymerization may performed also in the presence of a non-sunscreen functional co-dopant such as cosmetic ingredients or ingredients for coloring, leaching control transparency/opacity control, acidity/basicity control, hydrophobicity/hydrophilicity control.

The polymerization may be carried out under acidic, neutral or basic conditions for forming a porous gel, xerogel (dry gel) or colloidal suspension.

The present invention relates to a method for the protection of body tissues and other surfaces from UV radiation comprising coating said body tissues or surfaces with the sol-gel matrix entrapping sunscreen ingredients as described, and to cosmetic, pharmaceutical or industrial mixtures and compositions containing at least one type of doped sol-gel particle as described which is incorporated into a cosmetic or other vehicle to be applied topically to body tissues or to other surfaces.

DETAILED DESCRIPTION OF THE INVENTION

The present invention relates to sunscreen-doped sol-gel materials useful for protecting body tissues and other surfaces from ultra violet (UV) radiation, to a method for preparing said sunscreens and to a method for protecting body tissues and other surfaces from UV radiation, using the said sunscreens. In the present invention sol-gel matrices are generated by hydrolysis and condensation-polymerization of metal and semi-metal alkoxide monomers to which sunscreen molecules are added either prior to or after hydrolysis of the monomer, followed, if needed, by a pH change and by gelation. The resulting sunscreen-doped sol-gel materials can be obtained in almost any shape and may be applied, as dispersions or powders, to body tissues or other surfaces, thereby achieving protection of the body tissues or surface against damaging effects of the sun radiation, without having undesirable direct contact between the sunscreening chemical ingredients and the body tissues.

As opposed to any of the sunscreens known today, the sunscreen-doped sol-gel matrices of the present invention have the following advantages:

The sol-gel matrix is transparent to the UV range above 250 nm, thus allowing the UVA and UVB light to penetrate the sol-gel particle and interact with the entrapped sunscreen molecule.

The sol-gel matrix is thermally and photochemically stable (in contrast to plastic carriers), easily withstanding the normal duration of exposure to sunlight and much beyond it.

The preparation of sunscreen-doped sol-gel matrices is simple; direct physical entrapment in the course of the sol-gel polymerization is possible and no reaction with the sunscreen molecule itself is needed.

The method of the present invention is not limited to the type of sunscreen ingredients used because any sunscreen molecule can be entrapped.

Points which are important for cosmetic preparations:

The sol-gel matrix can remain visibly transparent when applied on human tissues, as, for instance, in the case of $SiO_2$ sol-gel matrix.

Sunscreen-doped sol-gel particles can be obtained in various sizes, including downsizing to sub-micron levels. The particle can be prepared in various shapes, including spherical particles which are preferable for smooth contact with the skin. Practically any desired shape and form, from microscopic to macroscopic, is attainable.

The hydrophobicity/hydrophilicity ratio of the sol-gel particles surface can be controlled by the suitable choice of the monomers (e.g., using trialkoxy silane derivatives). Likewise, the acidity/basicity of the particles can be controlled.

The entrapped sunscreen molecules are not in direct contact with the skin. Each doped sunscreen molecule or particle is isolated in an individual cage, thus avoiding ground state or photochemical interactions with impurities, photodecomposition products, adjacent sunscreen molecules or other ingredients of the cosmetic vehicle. As a consequence, a sunscreen cosmetic preparation with a broad absorption spectrum can be obtained by the incorporation of at least two types of sunscreen-doped sol-gel particles, either by co-entrapment or by entrapment in different particles, which differ in their UV spectra. Since the doped sunscreen molecules have improved thermal and photochemical stability on exposure to sunlight, the shelf life of these materials and their cosmetic preparations or mixtures for other use, increases.

No leaching occurs of the trapped sunscreen agent from the matrix into the cosmetic vehicle.

The sunscreen-doped sol-gel matrix may have a broad absorption spectrum, encompassing both the UVA and UVB regions, if the doped sunscreens differ in their UV spectra. Due to their complete matrix isolation the entrapped sunscreens do not color or discolor skin and do not stain clothes. Also, the entrapped sunscreens are odorless when applied on skin or hair.

No deposition of sunscreen crystals is possible. Crystallization is a major cause for the need to use high sunscreen concentrations for desired sun protection factor (SPF) values.

The small particles of the doped sol-gel material blend optimally in cosmetic preparations.

Sol-gel matrices, such as silica, are non-allergenic and biocompatible. When the sunscreen cosmetic vehicle is washed off the body, the entrapped sunscreen is markedly more environmentally friendly than the free molecule, which becomes a pollutant. Silica is safe to the environment and so is the molecule entrapped within it.

The sol-gel matrix is basically obtained by condensation-polymerizing of monomers of which at least one monomer is selected from the group consisting of metal alkoxides, semi metal alkoxides, metal esters, semi metal esters and from monomers of the formula M(R)n(P)m, wherein M is a metallic or semi metallic element, R is a hydrolyzable substituent, n is an integer from 2 to 6, P is a non polymerized substituent and m is an integer from 0 to 6. The metallic or semi metallic element may be silicon, titanium, zinc, aluminum or zirconium, the hydrolyzable substituent may be from the group of alkoxides, aryloxides, carboxylic esters, acyloxy groups, diketonato groups, hydrolizable aza groups and chlorine and the non polymerized substituent may be used for coloring, leaching control transparency/opacity control, acidity/basicity control or hydrophobicity/hydrophilicity control or may be a sunscreen moiety or derivative.

The non-sunscreen co-dopants may be cosmetic ingredients or for coloring, leaching control, transparency/opacity control, acidity/basicity control, hydrophobicity/hydrophilicity control.

Examples of suitable monomers are for example, the alkoxysilanes (such as tetramethoxysilane, tetraethoxysilane, allyl-trimethoxysilane etc.) resulting in silica-type ($SiO_2$) sol-gel glasses. Other preferred monomers are those which lead to the formation of ZnO and $TiO_2$ sol-gel matrices (e.g. zinc di-t-butoxide and titanium triisopropoxide).

The polycondensation is associated with gelation of a sol, which after drying is densified by a mild heat to form a solid matrix called xerogel. The optimal time to add the sunscreen molecules is either prior to or after hydrolysis of the monomer, followed, if needed, by a pH change, which is then followed by gelation. The properties of the final solid matrix are determined by the chemical and physical conditions during the preparation process, e.g. the ratio of metal/water (e.g. silane/water), the pH, the absence or presence of catalysts, the temperature, the drying time and the incorporation of organic additives such as surface active agents. The doped material can be obtained in almost any shape, including spherical particles which are preferable for smooth contact with the skin.

Methods for obtaining fine dispersions and powders include: grinding; preventing the sol from gelation by dilution; pH changes; addition of surfactants; spraying techniques; and controlled growth, as is taught in the general field of colloids (L. H. Clint et al., Faraday Discuss. 95, 219, 1993). Multilayered particles are likewise obtainable.

The said invention will be further illustrated by the following experiments and examples. These experiments and examples do not intend to limit the scope of the invention but to demonstrate and clarify it only.

In a typical procedure, mixtures containing the alkoxysilane monomer (typically tetraethoxysilane or tetramethoxysilane (TMOS)) and water, are prepared at different ratios of silane/water/alcohol (such as ethanol or methanol). Examples for such mixtures are those containing 18 mmol of TMOS, 50 mmol of methanol and either 18 mmol or 72 mmol of distilled water. The mixtures can be made to polymerize with either basic or acidic catalysts. In a typical case, acid catalysis is induced by adding 0.425 mmol of HCl. At the sol stage, 0.10 to 0.64 mmol of the sunscreen are added, depending on the desired SPF (sunscreen materials are usually at concentrations suitable for SPF values between 2 and 50), any desired sunscreen can be added at this stage, with typical examples being para-aminobenzoic acid (PABA) as a representative of the para amino benzoate sunscreens and octylmethoxycinnamate as an example of the cinnamate sunscreens. Other sunscreens usable at this stage are the salicylates, the benzophenones family, anthranilates, dibenzoylmethanes, camphores, metallic complexes and metal oxides.

Gelation is carried out at room temperature in a glass bottle covered with aluminum foil. After gelation takes place the aluminum foil is perforated, allowing slow evaporation of the solvent until dried xerogels are formed. The dried material is then ground to a fine powder. The doped xerogel microparticles can be coated with a second layer of sol-gel materials by dispersing in a mixture of TMOS/water/methanol with molar ratios 1/4/2.8, respectively, and stirring for six hours. The particles are seperated and dried under vaccume for 10 hours at a temperature of 353K.

Leaching tests were preformed by taking samples of 0.1–0.15 gr of each type of the doped particles and immersing in a flask containing 4 ml of methanol. The flask was covered and stirred for two hours at room temperature. The immersed particles were separated and dried for 10 hours at 323K. The entrapment proved to be leach proof and photostable, following prolonged exposure to sunlight (typically 7 hours).

What is claimed is:

1. Sunscreen-doped sol-gel material useful for protecting body tissues from sunlight radiation, wherein the body tissues are selected from the group consisting of skin, nails and hair, and wherein the sunscreen-doped sol-gel material comprises a sol-gel matrix and at least one chemical sunscreen capable of absorbing UV radiation in the range above 250 nm.

2. Sunscreen-doped sol-gel material according to claim 1, wherein the chemical sunscreen is selected from the group consisting of para-aminobenzoates, salicylates, cinnamates, benzophenones, anthranilates, dibenzoylmethanes and camphores.

3. Sunscreen-doped sol-gel material according to claim 1, wherein the sol-gel matrix is transparent to the UV radiation in the range above 250 nm, covering the UVA and UVB regions.

4. Sunscreen-doped sol-gel material according to claim 1, wherein the sol-gel matrix is in the form of particles, either dried or dispersed as a sol.

5. Sunscreen-doped sol-gel material according to claim 4, wherein the particles are 0.01–100 microns in diameter.

6. Sunscreen-doped sol-gel material according to claim 1, wherein the sol-gel matrix is in the form of a thin film or a thin coating.

7. Sunscreen-doped sol-gel material according to claim 1, wherein the sol-gel matrix is in the form of a monolith.

8. A method for the preparation of a sunscreen-doped sol-gel material comprising condensation-polymerizing of at least one monomer selected from the group consisting of metal alkoxides, semi-metal alkoxides, metal esters, semi-metal esters and monomers of the formula $M(R)n(P)m$, wherein M is a metallic or semi-metallic element, R is a hydrolyzable substituent, n is an integer from 2 to 6, P is a non-polymerizable substituent or a sunscreening moiety and m is an integer from 0 to 6, in the presence of at least one chemical sunscreen ingredient, resulting in the entrapment of said at least one chemical sunscreen ingredient within a formed sol-gel matrix of said sol-gel material.

9. A method according to claim 8, wherein the at least one chemical sunscreen ingredient is added after hydrolysis of the monomer, followed by a pH change and gelation.

10. A method according to claim 8, wherein the at least one chemical sunscreen ingredient is added to the polymerizing mixture prior to hydrolysis of the monomer.

11. A method according to claim 8, wherein the polymerization is performed in the presence of a non-sunscreen functional co-dopant.

12. A method according to claim 8, wherein the polymerization is carried out under acidic, neutral or basic conditions for forming a porous gel, xerogel (dry gel) or colloidal suspension.

13. A method according to claim 8, wherein the metallic or semi-metallic element is selected from the group consisting of silicon, titanium, zinc, aluminum and zirconium, and the hydrolyzable substituent is selected from the group consisting of alkoxides, aryloxides, carboxylic esters, acyloxy groups, diketonato groups, hydrolyzable aza groups and chlorine and the non-polymerizable substituent is selected from the group consisting of a coloring ingredient, leaching control ingredient, transparency/opacity control ingredient, acidity/basicity control ingredient, hydrophobicity/hydrophilicity control ingredient and sunscreen moiety.

14. A method according to claim 8, wherein the chemical sunscreen ingredient is selected from the group consisting of para-aminobenzoates, salicylates, cinnamates, benzophenones, anthranilates, dibenzoylmethanes and camphores.

15. A method according to claim 11, wherein the non-sunscreen functional co-dopant is selected from the group consisting of a cosmetic ingredient, coloring ingredient, leaching control ingredient, transparency/opacity control ingredient, acidity/basicity control ingredient and hydrophobicity/hydrophilicity control ingredient.

16. A method according to claim 15, wherein the cosmetic ingredient is a perfume.

17. A method according to claim 8, wherein the sol-gel material is obtained as a fine dispersion or as a powder by grinding or by stopping the sol from gelation by dilution or by pH changes or by adding surfactants or by using spraying techniques or by using controlled growth.

18. A method according to claim 8, wherein the chemical sunscreen ingredient is employed at a concentration suitable to achieve SPF values of the resulting sunscreen-doped sol-gel material between 2 and 50.

19. A method for the protection of body tissues from UV radiation comprising coating said body tissues with the sunscreen-doped sol-gel material of claim 1.

20. A cosmetic or pharmaceutical composition containing at least one sunscreen-doped sol-gel material of claim 1 incorporated into a cosmetic or other topical vehicle to be applied topically to body tissues.

* * * * *